(12) United States Patent
Hausheer et al.

(10) Patent No.: US 6,225,295 B1
(45) Date of Patent: May 1, 2001

(54) METHOD OF TREATING ACETAMINOPHEN OVERDOSE

(76) Inventors: Frederick H. Hausheer, 203 Kendall Pkwy., Boerne, TX (US) 78229; Seetharamulu Peddaiahgari, 1207 Fawn Haven, San Antonio, TX (US) 78248

( * ) Notice: Subject to any disclaimer, the term of this patent is extended or adjusted under 35 U.S.C. 154(b) by 0 days.

(21) Appl. No.: 09/671,792

(22) Filed: Sep. 27, 2000

(51) Int. Cl.$^7$ .................. A61K 31/185; A61K 31/28; A61K 31/255; A61K 31/662; A61K 31/663
(52) U.S. Cl. ............ 514/108; 514/127; 514/492; 514/517; 514/578
(58) Field of Search ................. 514/108, 127, 514/492, 517, 578

(56) References Cited

U.S. PATENT DOCUMENTS 5,661,188 * 8/1997 Weissman et al. ............. 514/711

OTHER PUBLICATIONS

The Merck Index (12th edition), p. 16, 1996.*

* cited by examiner

Primary Examiner—Phyllis G. Spivack
(74) Attorney, Agent, or Firm—Thomas J. Dodd

(57) ABSTRACT

A method of treating patients suffering from acetaminophen overdose is disclosed. The method comprises administering to a patient in need of treatment an effective amount of a thiol or reducible disulfide compound according to the formula set forth in the specification.

4 Claims, No Drawings

METHOD OF TREATING ACETAMINOPHEN OVERDOSE

FIELD OF THE INVENTION

This invention relates to a method for treating a patient suffering from overdose of acetaminophen. The method involves administering an effective amount of a disulfide or thiol-containing compound to a patient suffering from acetaminophen overdose.

BACKGROUND OF THE INVENTION

Acetaminophens are mainly over the counter pain relief medications, and are perhaps the most widely used drugs in the world. One of the most popular brands of the drug is Tylenol®. Acetaminophen is generally regarded as safe for use, although long-term adverse effects can include GI ulcers, nephropathy, anemia, liver damage, and other effects.

Adverse effects from accidental overdose can be potentially life threatening and include hepatic necrosis and nephropathy. The risk is increased significantly for chronic alcoholics, for persons who have recently ingested large amounts of alcohol, and for persons with impaired liver or kidney function.

Rapid treatment is necessary in the event of overdose, and currently includes supportive measures, and if overdose has been in the previous 24 hours, oral or IV dosing with acetylcysteine in antidotal amounts. IV administration is often preferred because oral administration of acetylcysteine often causes adverse GI effects like nausea and vomiting, which combined with the GI effects of acetaminophen overdose, can limit uptake of the antidote and impede recovery of the patient.

Mesna (sodium 2-mercaptoethene sulfonate) and dimesna (disodium 2,2'-dithiobis ethane sulfonate) are known therapeutic compounds that have heretofore demonstrated a wide variety of therapeutic uses. Both mesna and dimesna have been shown to be effective protective agents against certain specific types of toxicity associated with the administration of cytotoxic drugs used to treat patients for various types of cancer.

In particular, mesna has been used with some success in mitigating the toxic effects of cytotoxic agents such as ifosfamide, oxazaphosphorine, melphalane, cyclophosphamide, trofosfamide, sulfosfamide, chlorambucil, busulfan, triethylene thiophosphamide, triaziquone, and others, as disclosed in U.S. Pat. No. 4,220,660, issued Sep. 2, 1980.

The near absence of toxicity of dimesna further underscores the usefulness of this compound, as large doses can be given to a patient without increasing the risk of adverse effects from the protective agent itself.

Further, pharmacological profiles of each compound indicate that, if proper conditions are maintained, mesna and dimesna do not prematurely inactivate primary therapeutic drugs to a significant degree. Thus, neither compound will significantly reduce activity of the chemotherapeutic agent, and in many cases, act to potentiate the effect of the main drug on targeted cancer cells.

The molecular structures of both mesna and dimesna are shown below as Structure I and Structure II respectively.

(I)

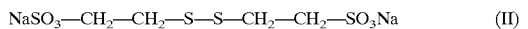

(II)

As shown, dimesna is a dimer of mesna, with the optimum conditions for oxidation occurring in the slightly basic (pH ~7.3), oxygen rich environment found in blood plasma. In mildly acidic, low oxygen conditions, in the presence of a reducing agent such as glutathione reductase, conditions prevalent in the kidneys, the primary constituent is mesna.

Mesna acts as a protective agent for a number of cytotoxic agents by substituting a nontoxic sulfhydryl moiety for a toxic hydroxy (or aquo) moiety. This action is particularly evidenced in the coadministration of mesna and oxazaphosphorine, and in the administration of dimesna along with certain platinum agents and/or taxanes.

Dimesna, as well as some analogues, have excellent toxicity profiles in mammalian species. In fact, dimesna has been administered intravenously to mice and dogs in doses higher than the accepted oral $LD_{50}$ for common table salt (3750 mg/kg), with no adverse effects. Dimesna has also been administered to humans in doses exceeding 40 g/m², with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration, usually a hydroxy, aquo or superoxide is located. Mesna also tends to form conjugates with naturally occurring biochemicals that contain a free thiol moiety, such as cysteine, glutathione, homocysteine, and others.

Dimesna and other disulfides can be activated intracellularly by glutathione reductase, a ubiquitous enzyme, thereby generating high concentrations of intracellular free thiols. These free thiols act to scavenge the free radicals and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, radiation exposure, chemical agent exposure, and other uses.

Mesna, dimesna, and analogues thereof are synthesized from commonly available starting materials, using acceptable routes well known in the art. One such method involves the two-step, single pot synthetic process for making dimesna and like compounds of the following formula:

wherein:

$R_1$ is hydrogen, X-lower alkyl, or X-lower alkyl-$R_3$;

$R_2$ is -lower alkyl-$R_4$;

$R_3$ and $R_4$ are each individually $SO_3M$ or $PO_3M_2$;

X is absent or X is sulfur; and

M is an alkali metal.

The process essentially involves a two-step single pot synthetic process, which results in the conversion of an alkenyl sulfonate salt or acid to the desired formula I compound. The process in the case of mesna is a single step process that converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well known and documented in the prior art, may be employed to make either mesna or dimesna, or derivatives and analogues thereof.

SUMMARY OF THE INVENTION

This invention involves the administration of an effective amount of a compound of formula I, below, for treatment of acetaminophen overdose.

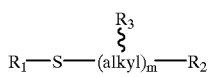
(I)

wherein:

$R_1$ is hydrogen, lower alkyl or

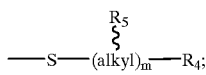

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

Each m is individually 1, 2, 3, 4, 5 or 6 with the proviso that if m is 1, then $R_3$ is hydrogen; and M is hydrogen or an alkali metal ion; or a pharmaceutically acceptable salt thereof.

Effective amounts of the formula I compound to be administered according to the method of this invention are variable, and depend upon the individual patient's response. However, due to the excellent toxicity profile of the formula I compounds, large amounts of drug may be administered, such as by continuous IV drip, without risk of untoward side effects commonly associated with other drugs used to treat this condition.

Accordingly, it is an object of this invention to provide for a method of safely and effectively treating acetaminophen overdose.

Another object is to provide a method of treating acetaminophen overdose by administration of a thiol or reducible disulfide to the patient desirous of treatment.

Other objects will become apparent upon a reading of the following description.

DESCRIPTION OF THE PREFERRED EMBODIMENTS

The preferred embodiments herein described are not intended to be exhaustive or to limit the invention to the precise form disclosed. They are chosen and described to explain the principles of the invention, and its application and practical use to best enable others skilled in the art to follow its teachings.

The method of this invention involves the administration of an effective amount of a formula I compound to a patient suffering from acetaminophen overdose. The effective amount of the formula I compound will necessarily depend upon the individual patient's response. Since the formula I compounds are essentially nontoxic and cleared rapidly from the patient's body, large amounts of drug can be safely administered.

The preferred dosage to treat acetaminophen overdose may be as low as 0.1 mg/kg up to 3,000 mg/kg. For parenteral administration, the formula I compound is dissolved in a suitable solvent, most preferably water, to produce a solution. One or more pharmaceutically acceptable excipients may also be added to provide for an elegant formulation. The formulation may also be incorporated into a continuous delivery device, such as an intrathecal pump or similar device.

For oral administration the formula I compound is preferably combined with one or more pharmaceutically acceptable excipients, fillers and/or diluents. Oral dosage forms may include pills, caplets, tablets, and others. Alternatively, the formula I compound may be contained in a deglutable container such as a gelatin capsule or the like. Since the half-life of the formula I compound is usually short, if the formula I compound is to be administered orally, then extended release dosage forms are most preferred.

The formula I compounds are hypothesized to work by binding to certain toxic metabolites of the acetaminophen, making them more water soluble and facilitating elimination through the urine.

Administration of the formula I compound should be made as soon as possible following diagnosis of acetaminophen overdose, preferably within 24 hours after ingestion, most preferably within 8 hours after ingestion. Preferred initial dose is between 10 mg/kg and 1000 mg/kg. High doses may be repeated ad libitum until positive results are achieved.

Careful observation and analysis is performed regularly after diagnosis and throughout treatment as per accepted medical procedures for treating patients for acetaminophen overdose. Dose rate may be altered depending upon the patient's response.

Also, due to the excellent safety profile, additional doses of the formula I compound may be administered safely if the initial dose period does not produce a positive response. Treatment may be repeated as often as necessary.

It is understood that the above description is in no way limiting of the invention, which may be modified within the scope of the following claims.

What is claimed is:

1. A method of treating acetaminophen overdose in a patient afflicted therewith, said method comprising administering to the patient an antidotal amount of a compound of formula I:

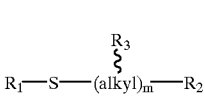
(I)

wherein:

$R_1$ is hydrogen, lower alkyl or

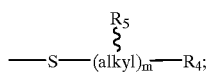

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

Each m is individually 1, 2, 3, 4, 5 or 6 with the proviso that if m is 1, then $R_3$ is hydrogen; and M is hydrogen or an alkali metal ion; or a pharmaceutically acceptable salt thereof.

2. The method of claim 1 wherein the effective amount of the formula I compound administered is from 0.1 mg/kg of body weight to 3,000 mg/kg of body weight.

3. The method of claim 1 wherein the compound is administered orally.

4. The method of claim 1 wherein the compound is administered subdermally or parenterally.

* * * * *